(12) United States Patent
Wahlig et al.

(10) Patent No.: US 6,689,375 B1
(45) Date of Patent: Feb. 10, 2004

(54) RESORBABLE BONE IMPLANT MATERIAL AND METHOD FOR PRODUCING THE SAME

(75) Inventors: Helmut Wahlig, Darmstadt (DE); Elvira Dingeldein, Dreieich (DE); Edgar Wüst, Rodgau (DE); Christoph Sattig, Dieburg (DE)

(73) Assignee: Coripharm Medizinprodukte GmbH & Co. KG, Dieburg (DE)

( * ) Notice: Subject to any disclaimer, the term of this patent is extended or adjusted under 35 U.S.C. 154(b) by 77 days.

(21) Appl. No.: 10/129,753

(22) PCT Filed: Oct. 14, 2002

(86) PCT No.: PCT/EP00/10133

§ 371 (c)(1),
(2), (4) Date: Jun. 5, 2000

(87) PCT Pub. No.: WO01/34216

PCT Pub. Date: May 17, 2001

(30) Foreign Application Priority Data

Nov. 9, 1999 (DE) .......................................... 199 53 771

(51) Int. Cl.[7] .................................................. A61F 2/00
(52) U.S. Cl. ........................ 424/426; 424/423; 424/424; 424/489

(58) Field of Search ............................... 623/19, 17, 12; 424/426, 423; 523/212; 501/1

(56) References Cited

U.S. PATENT DOCUMENTS

| | | | | |
|---|---|---|---|---|
| 4,778,834 A | * | 10/1988 | Murray | 523/212 |
| 5,614,206 A | * | 3/1997 | Randolph et al. | 424/426 |
| 6,013,591 A | * | 1/2000 | Ying et al. | 501/1 |

FOREIGN PATENT DOCUMENTS

| | | |
|---|---|---|
| EP | 0 159 087 | 10/1985 |
| EP | 0 159 089 | 10/1985 |
| GB | 2 323 083 | 9/1998 |

* cited by examiner

Primary Examiner—Thurman X. Page
Assistant Examiner—Micah-Paul Young
(74) Attorney, Agent, or Firm—Norris McLaughlin & Marcus

(57) ABSTRACT

The powdery component of the implant material consists essentially of a mixture of hydroxyl apatite powder and calcium sulfate powder, wherein the hydroxyl apatite powder consists of synthetically prepared, precipitated crystalline nanoparticles of high purity, which have a crystal size of 10–20 nm width and 50–60 nm length.

The specific absorbing BET surface area of the nanocrystals is preferably 100–150 $m^2/g$.

26 Claims, No Drawings

RESORBABLE BONE IMPLANT MATERIAL AND METHOD FOR PRODUCING THE SAME

BACKGROUND OF THE INVENTION

The invention relates to resorbable bone implant material prepared from a powdery component containing hydroxyl apatite and a liquid, as well as a method for preparing the same.

The importance of bone replacement materials, in particular in the areas of orthopedics, traumatology, cranial, dental and facial surgery, and orthodontics is still increasing. Significant areas of application—both in human medicine as in veterinary medicine—are, for example, the closing of large bone defects associated with comminuted fractures as well as the attachment of small bone fragments, the filling of bone defects resulting from bone cysts and after removal of bone tumors, the filling of voids caused by chronic osteomyelitis, applications associated with material loss on alveolis and jaw bones and the use as a carrier material, for example, for antibiotics, cytostatic, and osteogenic materials. The number of applications of bone replacement materials which increases worldwide year-to-year relates directly to their broad areas of indications. Several reasons therefor are the increasing life expectancy, the increasing industrialization, the increasing traffic density and steadily improving surgical techniques which allow any increasingly broader use of these materials. The need for bone replacement materials is so great because the materials which are best suited, namely autogenic spongy bone, are available only in limited quantities. In addition, their use requires a second, additional surgical procedure subject to the entire range of medical-surgical risks of any surgical procedure, whereby the newly created defects must in most cases be filled in again—with a bone replacement material.

Allogenic bones—which represent the next best implant material—can almost never be used today due to the high-risk for transmission of infectious substances, such as hepatitis and HIV virus, or of the Kreutzfeld-Jacob disease. Moreover, providing an equivalent tested and safe material, as well as operating bone banks require financial outlays that are often beyond reach.

Bone replacement materials which satisfy the stringent biological and chemical-physical requirements, are hence a medical and economical necessity and the development goal of several research groups.

Among the many implant materials that have been developed over the years, there were several that have found widespread application and which satisfy more or less today's medical and regulatory requirements for medical products. However, these products do not always meet the requirements expected from such medical products, namely availability, purity, reproducibility, standardizability, physical-chemical stability or compatibility. More frequently used today are, in particular, hydroxyl apatite ceramics, which are materials that are not broken down in the body, and calcium sulfate ("Plaster of Paris", hemihydrate of calcium sulfate) belonging to the group of resorbable bone replacement materials.

Hydroxyl apatite which can be implanted both in compact and in porous form, as a solid material or as granules or powder, is practically not broken down and therefore remains in the organism permanently and almost unchanged. With respect to integration with the bone, porous implants with an interconnecting system of voids which, if implanted with a pass fit in the form of blocks or cylinders, achieve the best results by forming an intimate connection with the host bone over the largest possible area. Corresponding animal experiments have shown that within several months, the implants that fill a bone defect are infused by newly formed bone that originates from the contact surfaces and covers the surface of the system of pores like a wallpaper cover.

The significant disadvantage of hydroxyl apatite is its inherent brittleness, so that implants of this type never reach the mechanical strength—in particular the elasticity—of the surrounding host bone, which severely limits its medical applications. Although it has been shown that porous hydroxyl apatite cylinders became mechanically stronger after the healing process than in their initial form, it was simultaneously observed that the webs between the pores had fissures and gaps, which could again indicate a weakening of the implant. Since these types of implants remain in the organism permanently, they also represent in the long run defects which can lead to a permanent weakening of the host bone and a permanent fracture risk, in particular in bone regions that are mechanically severely stressed.

On the other hand, the material hydroxide apatite itself biologically interacts with the host tissue in a rather positive way.

To get around the disadvantages of a non-resorbable bone replacement that remains intact even after complete integration into the bone, research focused during recent years increasingly on implant materials that can be broken down. In this field, in particular calcium sulfate has found a renaissance, considering that aside from several more recent publications, a first report appeared in 1892, wherein "Plaster of Paris" was used for filling of tuberculous and osteomyelitic bone defects.

Like hydroxyl apatite, calcium sulfate has advantageous biological properties. However, unlike hydroxyl apatite, depending on its shape and volume, calcium sulfate is very quickly broken down and resorbed in the organism within several weeks or months.

This actually desirable and advantageous feature is negated in that the implant tends to be broken down significantly faster than the bone can regrow from the implant bed. This causes voids to be formed once again which are then typically no longer filled by bone, but rather by connecting tissue.

WO 87/05521 A1 describes a bone implant material in form of a plastic, moldable mass for filling bone defects. The mass consists of sintered hydroxyl apatite granules with a grain size of 250–5000 μm, which is substantially insoluble and/or cannot be broken down in the organism, and calcium sulfate-hemihydrate. The materials described above are commercially available, but their manufacturing conditions, physical-chemical and medical properties and in particular their purity cannot be ascertained. The dry components are mixed together in the ratio of 70–60% to 30–40% and then mixed further with a suitable liquid (water, physiological sodium chloride solution) into a moldable paste which solidifies in situ after application. According to the description, the calcium sulfate dissolves quickly in the bone defect (within several days to several weeks). The voids which are formed between the hydroxyl apatite granules that are situated more or less loosely in the defect, should then enable the newly formed bone to grow into the voids. Due to accepted medical understanding of the physiological processes during bone healing, the aforedescribed product as well as the way in which it is applied appear to have problems in several aspects. The rapid dissolution of calcium sulfate, which has been promoted as an advantage, induces the risk that the calcium sulfate is dissolved faster than new bone can grow. In this case, connective tissue could grow around the hydroxyl apatite granules which are not connected to each other and therefore do not provide mechanical stability as an implant material, so that the defect would not be filled by bone. This risk also seems to manifest itself in a decrease of the compressive strength of the fill material by 53% after only two days in an in vivo experiment conducted in sodium chloride solution. The results of the described animal experiments are not convincing. For example, it was mentioned that "small defects (small holes)" occur in the rabbit tibia; these, however, are known to be filled by bone during the physiological repair processes without requiring additional filling. Also, the reported defects after tooth extraction on beagles were of small size. The defects were in both cases overgrown by gingiva after 7–10 days, with and without implant.

Two patents (EP 0 159 087 A1 and EP 0 159 089 A1) describe resorbable implant materials used as carriers of active ingredients for releasing drugs in bone or tissue. The materials are each composed of two components. In the first case, calcium sulfate and calcium carbonate powder in a ratio of 0.3 to 1.0 is mixed with a drug and thereafter mixed with water to form a paste. After the mass has solidified, it can be introduced into the organism, for example, as a carrier for antibiotics. By using calcium carbonate, the implant is broken down much more slowly than plaster (within several months), which should leave sufficient time for the healing process, i.e., to replace the implant, for example in a bone defect, with newly formed bone. In the second case, calcium sulfate is mixed with calcium monohydrogen phosphate and the dried mass is subsequently heated to 700° C. until the calcium hydrogen phosphate melts. The resulting micro-porous mass can be impregnated with the drugs and placed in the organism as a drug carrier. However, the chemical-physical and/or medical properties of the aforementioned powdery components were not specified.

Finally, the patent application GB 2 323 083 A describes the manufacture of an implant material for filling bone defects, wherein the implant material is composed of a mixture of sintered or non-sintered hydroxyl apatite granules with a grain size of 100–400–5000 μm and hydroxyl apatite powder with a grain size of 1–40 μm in a ratio of 1:0.1 to 1:1. This mixture is heated to 800–1200° C. either dry or as an aqueous suspension, optionally by adding dispersion promoters or binders. The fine powder connects the larger granules with each other during the sintering process, so that solid form bodies (blocks) can be produced, which can then be used for filling bone defects. Since irregular bone defects cannot be formfittingly filled with blocks, the blocks are crushed by applying finger pressure during application and thereby separated into the initial granules, which are then used to fill the defects. When present as sintered hydroxyl apatite, the implant material cannot be broken down in the organism. Based on current medical understanding, problems can arise when filling bone defects with separate larger granules due to the mechanical instability of the implant material. Permeation of bone into the implant is also doubtful, so that the method described in the above referenced patent appears to be without a logical foundation. The question has to be asked why solid form bodies, which by themselves are poorly suited for filling defects, are initially produced from granules by a complex production process, only to be later—just to compensate for this disadvantage—destroyed during application by producing and implanting again the initial granules.

SUMMARY OF THE INVENTION

It is an object of the invention to provide a resorbable implant material, in particular for use in surgery, orthopedics, traumatology and dentistry, which combines the advantages of hydroxyl apatite and calcium sulfate and simultaneously eliminates the associated disadvantages, as well as a method for producing such implant material.

DETAILED DESCRIPTION OF THE PREFERRED

The object is solved by the invention in that the powdery component consists essentially of a mixture of hydroxyl apatite powder and calcium sulfate powder, wherein the hydroxyl apatite powder consists of synthetically produced, precipitated crystalline nanoparticles of high purity with a crystal size of 10–20 nm width and 50–60 nm length.

The specific absorbing BET surface area of the nanocrystals is 100–150 $m^2/g$.

The implant material according to the invention does not need to be provided in form of solid form bodies to achieve a pass-fit implantation, because such "press fit" implantation has significant practical difficulties. Instead, the implant material can also be implanted in the form of a moldable mass that solidifies after application, which makes the application much easier and has also the advantage that defects with irregularly boundaries can be completely filled in. This type of defect filling can also prevent the undesirable growth of connecting tissue into the defects. Moreover, the material should also be applicable in the form of a granules and/or small or larger solid form bodies, in particular in the form of spheres or cylinders, because these shapes have proven successful in certain indications for filling defects. In addition, these shaped form pieces are suitable carriers for active ingredients, whereby the implant itself should in each case be able to be broken down and/or resorbable within a biologically suitable time.

The two components of the new bone replacement materials according to the invention, hydroxyl apatite and calcium sulfate, will now be described in more detail:

It has been shown that the requirement of the invention for a resorbable hydroxyl apatite is satisfied surprisingly well by a particular form of the hydroxyl apatite. The material of the invention is a hydroxyl apatite that, unlike any other hydroxyl apatite material used until now as an implant, is not exposed to a sintering process, but is produced synthetically by precipitation. The so produced material is also absolutely pure as a result of the particular production process and is available in the form of very small crystals (so-called nanoparticles). The crystal size of this material is 10–20 nm in width and 50–60 nm in length, and therefore approaches the size of the apatite crystals in human bones of 5–10 nm. The specific absorbing BET surface area of the nanocrystals is approximately 100–150 $m^2/g$.

A crystalline hydroxyl apatite material of this type is described in EP 0 664 133 B1. However, this patent claims an aqueous paste with a fraction of 18–36 wt. % of the aforedescribed hydroxyl apatite. Such paste has shown very good regenerative properties in animal experiments by stimulating autogenic bone healing. However, it was found to be necessary to cover the cylindrical defects with a cover after they were filled with the paste, so as to prevent the paste from escaping from the defect after application. Applying an aqueous paste has the disadvantage that the paste becomes more liquid due to secretion of blood and/or other bodily fluids, in particular when the defects are larger or shallow trough-like, and can thereby be washed out of the defect reservoir.

Conversely, with the implant material of the invention, a powder composed of hydroxyl apatite nanoparticles is used which, on one hand, has the beneficial biological properties of nanoparticles which, unlike sintered hydroxyl apatite crystals which are not broken down in the body, can be fully resorbed, and on the other hand, fill and close the bone defects until the implant is physiologically resorbed slowly and replaced in time by newly formed autogenic bone.

It has been observed that it is particularly advantageous to combine synthetically prepared calcium sulfate with the hydroxyl apatite nanoparticles for the purpose of strengthening the apatite powder or the formation of pellet-type materials, such as granules and form body for filling defects in special medical indications, or as carrier for active ingredients. Unlike the conventionally applied "Plaster of Paris" material which occurs naturally, the material of the invention can advantageously be manufactured reproducibly—with essentially 100% purity and a very high and uniform quality. The material of the invention also does not contain any harmful components, additives or impurities that would be objectionable in a medical or physical-chemical sense, so that the material can be standardized and, in particular, meet the regulatory guidelines for medical products and the terms of the Pharmacy Act.

The calcium sulfate powder used with the implant material of the invention therefore consists of a synthetically produced α-subhydrate (bassanite) with $n*H_2O$ (whereby $n<1$, approximating 0.5), with an optional additional fraction of 5–10% calcium oxide. The specific absorbing BET surface area is 1.8–2.7, preferably 2.0–2.3 $m^2/g$.

Surprisingly, it has been experimentally observed in materials with different BET surface areas that a ratio of the specific surface areas of approximately 150:2 $m^2/g$ for the combined powder fractions of hydroxyl apatite and calcium sulfate is particularly advantageous for achieving the desired therapeutic and particularly the biological effects. This applies both to the mass that solidifies in situ as well as to the use of pellet-type form body, granules, spheres, cylinders, etc.

It has also been found that the mass that after implantation solidifies in the filled-in defects advantageously consists of a hydroxyl apatite nanoparticle powder with a fraction of 15–45%, preferably 20–30%, of the calcium sulfate powder of the invention. Such powder mix is processed before application with 1–2 parts water into a viscous mass which after implantation solidifies in situ. Animal experiments have shown that after such a mass is applied, it functions as an osteo-conductive matrix, promoting the invasion of blood vessels and the growth of bone-forming cells. The matrix then begins to break down in the bone defect and is resorbed, whereby this material strongly stimulates the formation of new bone tissue in the defect region and in particular initiates a rapid neoangiosesis which is essential for any subsequent bone consolidation. It came as a complete and unexpected surprise and contrary to expectations from working with other hydroxyl apatite implants, that early stages of the bold-forming cells migrate much earlier, already after approximately 10 days, through the newly formed capillaries to the location of the implant, where they settle in the region of the apatite nanocrystals and form new bone. The new bone is initially formed mostly as plexus bone, but subsequently changes into lamella bone. In this way, the typical time for rebuilding a bone defect with a diameter of 6 mm in rabbits could be shortened from 5–6 weeks after filling with a porous sintered ceramic material to 2.5–3 weeks after filling with a combination of apatite nanoparticles and calcium sulfate. The large fraction of 70–80 wt. % of nanoparticles in the implant mass thereby prevents the calcium sulfate from breaking down quickly, so that the rate of resorption of the implant can be closely matched to the physiological rate of the formation of new bone.

When using the material combination of the invention, this biological process is characterized by an exceptional compatibility of the implant material, as evidenced mainly by the absence of an inflammatory reaction and the formation of seropus. Those reactions, and more particularly the frequently occurring seropus formation, frequently delay the healing process with other implant materials—in particular during the first 2 to 3 weeks—and hence also to a large extent delay the formation of new bone. Such episodes have frequently been described in connection with conventional calcium sulfate implants. One reason therefor is that plaster, in spite of decade-long clinical attempts, has never found a therapeutic use that was entirely satisfactory, which also prevented its widespread use. When looking for the underlying causes, the acidic pH value of the calcium sulfate in the range of pH=6 was suspected to have a significant effect on these processes.

Surprisingly, it has been observed that when the materials of the invention are combined, the nanoparticle powder moves the pH value to a neutral or slightly alkaline range and that this material shows a buffer effect. It has been known for a long time that the organism prefers a slightly alkaline pH value in biological processes that involve tissue regeneration and bone healing, which appears to be rather advantageous for the repair process. In particular, tissue irritation which is observed in an acidic environment and which delays the healing process, is eliminated which explains the surprisingly advantageous, rapid and superior healing properties of the material combination of the invention. Addition of a small fraction of 2–15 wt. % of calcium oxide in the calcium sulfate amplifies this effect even more by promoting a slightly alkaline pH value.

The paste made of nanoparticles, unlike conventional implant materials, has another significant advantage in that the bone replacement material of the invention can be readily distinguished in an x-ray image after implantation as a result of the specific combination of materials.

It has also been found that the material of the invention can also be injected into a bone defect through an applicator—like a syringe—having a suitably sized needle immediately after mixing, optionally also percutaneous under x-ray observation. The material then solidifies in the bone defect.

Instead of or in addition to a plastic mass, different indications in the surgery, orthopedics, dental surgery and traumatology may also advantageously employ previously solidified pellet-like material, i.e., form body such as granules, spheres, cylinders, prisms, cuboids, etc. of different size for filling and repairing defects.

It has been observed that the combination of apatite nanoparticles and calcium sulfate according to the invention can be used to produce such form body, which still retain their advantageous biological properties.

It has been found advantageous in many situations to combine implant materials with one or several suitable antibiotics, either to prevent infections following the surgical application of the material, or to safely apply such implants in the repair of osteomyelitic bone defects. Impregnating such bone replacement materials with other pharmaceutical ingredients and growth factors has also been described.

It has been observed that the combination of materials of the invention is particularly well adapted for incorporation of pharmaceutical ingredients. By mixing the two components with water, form body of different size and form can be produced which can subsequently be sterilized by a suitable method, such as for example by treatment with β or γ rays or by gassing with ethylene oxide. Irradiation with β or γ rays can be considered can also be used to sterilize the starting materials for the implant mass that solidifies in the organism.

Unlike conventional methods, wherein the active ingredients are for example added to the calcium sulfate powder or to the water which then enter the matrix when the material is prepared (DE 196 20 117 C1; EP 0 159 087 A1), it has been found to be advantageous to first prepare granules or form body of the material combination of the invention, before they are subsequently sterilized and impregnated under sterile conditions with suitable sterile solutions of active ingredients containing antibiotics or growth factors.

Surprisingly, a matrix can be obtained by using a particular mixing ratio of the two components of the invention and by taking into account the specified ratios of the corresponding BET surface areas mentioned above, as well as by using a standardized mixing process, wherein the matrix has a standardizable and reproducible water retention capacity between 46.6 and 68.3 wt. %. The matrix can then be impregnated with the active ingredient solutions in a straightforward and standardizable manner. Moreover, the controllable liquid retention makes it feasible to not only set narrow limits for the feed quantities supplied to the form body that are to be impregnated, but also to subsequently release the active ingredients—in vitro, and also in the biological environment after the implantation—reproducibly and over an extended time. As a result, such implant bodies can have a prophylactic as well as a therapeutic effect.

In addition, the implant system advantageously provides the attending physician with an implant that—as is the case with conventional materials—has not merely one particular active ingredient in only one particular concentration. Instead, the physician is able to select directly before the implantation from a palette of sterile active ingredient solutions in different concentrations the most beneficial and most suitable active ingredient for the particular indication, adapted to the individual clinical situation and, if necessary, to the bacteriologic findings for a particular patient. The attending physician himself can also impregnate the material under sterile conditions using a ready-made kit and then immediately implant the impregnated material. It will be understood that granules or form body can thereby be easily impregnated with combinations of active ingredient, which opens for the surgeon many therapeutic opportunities and new candidates for a targeted local application of active ingredients.

What is claimed is:

1. Resorbable bone implant material prepared from a powdery component containing hydroxyl apatite and from a liquid, wherein the powdery component consists essentially of a mixture of hydroxyl apatite powder and calcium sulfate powder wherein the BET surface area ratio of the mixture of apatite nanoparticles and calcium sulfate particles is approximately 150 m$^2$/g: 2 m$^2$/g, and that the hydroxyl apatite powder consists of synthetically produced, precipitated crystalline nanoparticles of high purity, which have a crystal size of 10–20 nm width and 50–60 nm length.

2. Implant material according to claim 1, wherein the specific absorbing BET surface area of the nanocrystals is 100–150 m$^2$/g.

3. Implant material according to claim 1, wherein the calcium sulfate powder consists of a synthetically prepared alpha-subhydrate of high purity (bassanite) with n*H$_2$O (wherein n<1 and approximately 0.5).

4. Implant material according to claim 3, wherein the specific absorbing BET surface area of the calcium sulfate particles is 1.8–2.7m$^2$/g, preferably 2.0–2.3 m$^2$/g.

5. Implant material according to claim 3, wherein the calcium sulfate powder contains an additional fraction of 2–15 wt. %, preferably 5–10 wt. %, calcium oxide.

6. Implant material according to claim 1, wherein the fraction of hydroxyl apatite powder in the powdery components is 85–55 wt. %, preferably 80–70 wt. %.

7. Implant material according to claim 1, wherein the powdery components is sterilized by β or γ radiation before its preparation.

8. Implant material according to claim 7, wherein the sterile powdery component is prepared with sterile water into an initially viscous and subsequently solidifying mass.

9. Implant material according to claim 8, wherein the fraction of the sterile water during preparation of the viscous mass is 100–200 wt. %, based on the weight of the powdery components.

10. Implant material according to claim 8, wherein the viscous mass has a slightly alkaline pH value in the range of pH 7.5–8.2.

11. Implant material according to claim 8, wherein the mass after preparation has a viscous plastic consistency.

12. Implant material according to claim 1, wherein the implant material is present in the form of granules having different grain sizes or in the form of form body, in particular spheres, cylinders, prisms or cuboids having different dimensions.

13. Implant material according to claim 12, wherein the powdery components are prepared with 100–200 wt. % distilled water, based on the weight of the powdery components, and solidified in molds.

14. Implant material according to claim 13, wherein the material that solidified in the molds is comminuted into a granular consistency.

15. Implant material according to claim 12, wherein the implant material is adjusted to a standardized reproducible water retention capacity.

16. Implant material according to claim 12, wherein the form body, after hardening, are sterilized by irradiation with β and γ rays or by gassing with ethylene oxide, and are packaged in sterile form.

17. Implant material according to claim 12, wherein the form body are impregnated before application with sterile pharmaceutical solutions containing active ingredients.

18. Implant material according to claim 17, wherein antibiotics or growth factors prepared a liquid form are provided as solutions containing active ingredients.

19. Implant material according to claim 17, wherein the form body are impregnated with a combination of two or more different solutions containing active ingredients.

20. Method for preparing a bone implant material from a powdery component containing hydroxyl apatite with water, wherein the powdery component is prepared by mixing of 85–55 wt. % hydroxyl apatite powder of synthetically produced precipitated nanoparticles of high-purity hydroxyl apatite having a crystal size of 10–20 nm width and 50–60 nm length with 15–45 wt. % calcium sulfate powder in form of a high-purity α-subhydrate with n*H$_2$O (wherein n<1 and approximately 0.5), and the produced powder mixture is prepared with a fraction of 100–200 wt. % sterile water into an initially viscous mass, which subsequently solidifies to form a body.

21. Method according to claim 20, wherein 5–10 wt. % calcium oxide powder is added to the calcium sulfate powder before or during mixing with the hydroxyl apatite powder.

22. Method according to claim 20, wherein the powdery component is sterilized before its preparation by irradiation with β or γ rays.

23. Method according to claim 20, wherein the initially prepared viscous mass is introduced into molds, solidified therein and removed from the molds as pellet-like form body.

24. Method according to claim 23, wherein the form body are sterilized by irradiation with β or γ rays or by gassing with ethylene oxide and subsequently packaged in sterile form.

25. Method according to claim 23, wherein the sterile form body are impregnated before the application with a pharmaceutical solution containing active ingredients.

26. Method according to claim 23, wherein the sterile form body are impregnated before the application with a combination consisting of two or more pharmaceutical solutions containing different active ingredients.

* * * * *